United States Patent [19]
Handley et al.

[11] Patent Number: 5,900,421
[45] Date of Patent: May 4, 1999

[54] METHODS AND COMPOSITIONS FOR TREATING ALLERGIC ASTHMA AND DERMATITIS USING DESCARBOETHOXYLORATADINE

[75] Inventors: Dean A. Handley, Westborough; Paul D. Rubin, Sudbury, both of Mass.

[73] Assignee: Sepracor Inc., Marlborough, Mass.

[21] Appl. No.: 08/799,605

[22] Filed: Feb. 11, 1997

[51] Int. Cl.$^6$ ..................................................... A61K 31/44
[52] U.S. Cl. .......................... 514/290; 514/826; 514/864
[58] Field of Search .................................. 514/290, 826, 514/864

[56] References Cited

U.S. PATENT DOCUMENTS

| | | | |
|---|---|---|---|
| 4,659,716 | 4/1987 | Villani et al. | 514/290 |
| 5,019,591 | 5/1991 | Gardner et al. | 514/461 |
| 5,089,496 | 2/1992 | Piwinski et al. | 514/253 |
| 5,595,997 | 1/1997 | Aberg et al. | 514/290 |

FOREIGN PATENT DOCUMENTS

| | | |
|---|---|---|
| 0 288 640 | 11/1988 | European Pat. Off. . |
| WO 85/03707 | 8/1985 | WIPO . |
| WO 92/00293 | 1/1992 | WIPO . |
| WO 92/11034 | 7/1992 | WIPO . |
| WO 96/20708 | 7/1996 | WIPO . |

OTHER PUBLICATIONS

Anderson et al., "Adverse Drug Interactions Clinically Important for the Dermatologist," *Arch. Dermatol.*, 131:468–473 (1995).

Berthon et al., "In Vitro Inhibition, by Loratadine and Descarboxyethoxloratadine, of Histamine Release from Human Basophils, and of Histamine Release and Intracellular Calcium Fluxes in Rat Basophilic Leukemia Cells (RBL–2H3)," *Biochemical Pharmacology*, 47:(5), pp. 789–794 (1994).

Brandes et al., "Enhanced Cancer Growth in Mice Administered Daily Human–Equivalent Doses of Some $H_1$–Antihistamines: Predictive In Vitro Correlates," *J. Nat. Can. Inst.* Reports, 86:(10), pp. 770–775 (1994).

Kleine–Tebbe et al., "Inhibition of IgE–and non–IgE–mediated histamine release from human basophil leukocytes in vitro by a histamine $H_1$–antagonist, desethoxycarbonyl–loratadine," *J. Allergy Clin. Immunol.*, 93:(2), pp. 494–500 (1994).

Miadonna et al., "Inhibitory Effect of the $H_1$ Antagonist Loratadine on Histamine Release from Human Basophils," *Int. Arch. Allergy Immunol.*, (105), pp. 12–17 (1994).

Zhong et al., "HPLC–Bestimmung Von Loratadin und seinem aktiven Metaboliten Descarboethoxyloratadin in Humanplasma," *Pharmazie*, (49) H.10, pp. 736–739 (1994) (English abstract attached).

Lavrijsen et al., "The Interaction of Ketoconazole, Itraconazole and Erythromycin With the In Vitro Metabolism of Antihistamines in Human Liver Microsomes," Abstract 1233, *Eur. J. Allergy Clin. Immunol.*, 48, Suppl. 16, 34 (1993).

Van Peer et al., "Ketoconazole Inhibits Loratadine Metabolism in Man," Abstract 1234, *Eur. J. Allergy Clin. Immunol.*, 48, Suppl. 16, 34 (1993).

Quercia et al., "Focus on loratadine: A new second–generation nonsedating $H_1$–receptor antagonist," *Hosp. Formul.*, (28), pp. 137–153 (1993).

Product Insert CR–318/17597400 Jul. 1993 Schering Corporation (1992, 1993).

Brandes et al., "Stimulation of Malignant Growth in Rodents by Antidepressant Drugs at Clinically Relevant Doses," *Cancer Research*, (52), pp. 3796–3800 (1992).

Knowles, "Astemizole and Terfenadine — Induced Cardiovascular Effects," *Canadian J. Hosp. Pharm*, 45:(1) pp. 33, 37 (1992).

Parkinson et al., "Evaluation of Loratadine as an Inducer of Liver Microsomal Cytochrome P450 In Rats and Mice," *Biochemical Pharmacology*, 43:(10), pp. 2169–2180 (1992).

"Antihististamines," Chapter 16, *Side Effects of Drugs Annual*, 14, pp. 135–138, Elsevier Science Publishers (1990).

Clissold et al., "Loratadine A Preliminary Review of its Pharmacodynamic Properties and Therapeutic Efficacy," *Drugs*, 37, pp. 42–57 (1989).

"Antihististamines," Chapter 16, *Side Effects of Drugs Annual*, 12, pp. 142–143, Elsevier Science Publishers (1988).

Simons et al., "Astemizole — Induced Torsades de Pointes," *Lancet*, p. 624 (Sep. 10, 1988).

Temple et al., "Loratadine, an Antihistamine, Blocks antigen–and Ionophore — Induced Leukotriene Release From Human Lung In Vitro," *Prostaglandins*, 35:(4), pp. 549–554 (1988).

Hilbert et al., "Pharmacokinetics and Dose Proportionality of Loratadine," *J. Clin. Pharmacol.*, (27), pp. 694–698 (1987).

Craft, "Torsade de Pointes After Astemizole Overdose," *British Med. J.*, (292), p. 660 (1986).

Barnett et al., "Evaluation of the CNS properties of SCH 29851, a potential non–sedating antihistamine," *Agents and Actions*, 14:(5/6), pp. 590–597 (1984).

Wood, "Antimotion Sickness and Antiemetic Drugs," *Drugs*, (17), 17 pp. 471–479 (1979).

Cohen et al., "Meclizine and Placebo in Treating Vertigo of Vestibular Origion," *Arch. Neurol.*, (27), pp. 129–135 (1972).

*Primary Examiner*—Kimberly Jordan
*Attorney, Agent, or Firm*—Pennie & Edmonds LLP

[57] ABSTRACT

Methods utilizing descarboethoxyloratadine ("DCL"), for the treatment of allergic disorders, while avoiding the concomitant liability of adverse side-effects associated with other non-sedating antihistamines. Also included are methods for the treatment of allergic asthma using DCL and either a decongestant or a leukotriene inhibitor, while avoiding the concomitant liability of adverse side-effects associated with other non-sedating antihistamines. The invention also encompasses the administration of DCL in a nasal or oral spray.

18 Claims, No Drawings

METHODS AND COMPOSITIONS FOR TREATING ALLERGIC ASTHMA AND DERMATITIS USING DESCARBOETHOXYLORATADINE

1. FIELD OF THE INVENTION

The present invention relates to methods of treatment involving the administration of a therapeutically effective amount of a metabolic derivative of loratadine known as descarboethoxyloratadine.

2. DESCRIPTION OF THE RELATED ART

Loratadine is an antagonist of the H-1 histamine receptor protein. The histamine receptors H-1 and H-2 are two well-identified forms. The H-1 receptors are those that mediate the response antagonized by conventional antihistamines. H-1 receptors are present, for example, in the ileum, the skin, and the bronchial smooth muscle of man and other mammals.

Loratadine binds preferentially to peripheral rather than to central H-1 receptors. Quercia et al., Hosp. Formul. 28: 137–53 (1993). Loratadine has been shown to be a more potent inhibitor of serotonin-induced bronchospasm in guinea pigs than terfenadine. Id. at 137–38. Its anti-allergenic activity in animal models was shown to be comparable to that of terfenadine and astemizole. Id. at 138. However, using standard animal model testing, on a milligram by milligram basis, loratadine was shown to be four times more potent than terfenadine in the inhibition of allergic bronchospasm. Id. Moreover, loratadine's antihistaminic activity was demonstrated in humans by evaluation of the drug's ability to suppress wheal formation. Id. Clinical trials of efficacy indicated that loratadine is an effective H-1 antagonist. See Clissold et al., Drugs 37: 42–57 (1989).

Through H-2 receptor-mediated responses, histamine stimulates gastric acid secretion in mammals and the chronotropic effect in isolated mammalian atria. Loratadine has no effect on histamine-induced gastric acid secretion, nor does it alter the chronotropic effect of histamine on atria. Thus, loratadine has no apparent effect on the H-2 histamine receptor.

Loratadine is well absorbed but is extensively metabolized. Hilbert, et al., J. Clin. Pharmacol. 27: 694–98 (1987). The main metabolite, DCL, which has been identified, is reported to be pharmacologically active. Clissold, Drugs 37: 42–57 (1989). It is also reported as having antihistaminic activity in U.S. Pat. No. 4,659,716. This patent recommends an oral dosage range of 5 to 100 mg/day and preferably 10 to 20 mg/day.

Loratadine's efficacy in treating seasonal allergic rhinitis is comparable to that of terfenadine. Quercia et al., Hosp. Formul. 28: 137, 141 (1993). Loratadine also has a more rapid onset of action than astemizole. Id.

Clissold et al., Drugs 37: 42, 50–54 (1989) describes studies showing loratadine as effective for use in seasonal and perennial rhinitis, colds (with pseudoephedrine), and chronic urticaria. It has also been suggested that loratadine would be useful for the treatment of allergic asthma. Temple et al. Prostaglandins 35: 549–554 (1988).

Loratadine may also be useful for the treatment of motion sickness and vertigo. Some antihistamines have been found to be effective for the prophylaxis and treatment of motion sickness. See Wood, Drugs, 17: 471–79 (1979). Some antihistamines have also proven useful for treating vestibular disturbances, such as Meniere's disease, and in other types of vertigo. See Cohen et al., Archives of Neurology, 27: 129–35 (1972).

In addition, loratadine may be useful in the treatment of diabetic retinopathy and other small vessel disorders associated with diabetes mellitus. In tests on rats with streptozocin-induced diabetes, treatment by antihistamines prevented the activation of retinal histamine receptors which have been implicated in the development of diabetic retinopathy. The use of antihistamines to treat retinopathy and small vessel disorders associated with diabetes mellitus is disclosed in U.S. Pat. No. 5,019,591.

It has also been suggested that loratadine, in combination with non-steroidal antiinflammatory agents or other non-narcotic analgesics, would be useful for the treatment of cough, cold, cold-like and/or flu symptoms and the discomfort, pain, headache, fever, and general malaise associated therewith.

Many antihistamines cause adverse side-effects. These adverse side-effects include, but are not limited to, sedation, gastrointestinal distress, dry mouth, constipation or diarrhea. Loratadine has been found to cause relatively less sedation as compared with other antihistamines. Moreover, the incidence of fatigue, headache, and nausea was similar to those observed for terfenadine. See Quercia et al., Hosp. Formul. 28: 137,142 (1993).

Furthermore, compounds within the class of non-sedating antihistamines, including loratadine, astemizole, and terfenadine, have been known to cause other severe adverse electrophysiologic side-effects. These adverse side-effects are associated with a prolonged QT interval and include but are not limited to ventricular fibrillation and cardiac arrhythmias, such as ventricular tachyarrhythmias or torsades de pointes. Knowles, Canadian Journal Hosp. Pharm., 45: 33,37 (1992); Craft, British Medical Journal, 292: 660 (1986); Simons et al., Lancet, 2: 624 (1988); and Unknown, Side Effects of Drugs Annual, 12: 142 and 14: 135.

Quercia et al., Hosp. Formul. 28: 137, 142 (1993) noted that serious cardiovascular adverse side-effects, including torsades de pointes and other ventricular arrhythmias, were reported in "healthy" patients who received terfenadine concurrently with either ketoconazole or erythromycin. Quercia et al., also states that arrhythmias have also been reported with the concomitant administration of astemizole and erythromycin or erythromycin plus ketoconazole. Thus, he cautions against using loratadine concurrently with ketoconazole, itraconazole, and macrolides, such as erythromycin.

Additionally, it is also known that ketoconazole and/or erythromycin interfere with cytochrome P450, and thereby inhibit the metabolism of non-sedative antihistamines such as terfenadine and astemizole. Because of the interference with the metabolism of loratadine, there exists a greater potential for adverse interaction between loratadine or other non-sedating antihistamines and drugs known to inhibit cytochrome P450, such as but not limited to ketoconazole, itraconazole, and erythromycin.

In Brandes et al., Cancer Res. (52) 3796–3800 (1992), Brandes showed that the propensity of drugs to promote tumor growth in vivo correlated with potency to inhibit concanavalin A stimulation of lymphocyte mitogenesis. In Brandes et al., J. Nat'l Cancer Inst., 86(10): 771–775 (1994), Brandes assessed loratadine in an in vitro assay to predict enhancement of in vivo tumor growth. He found that loratadine and astemizole were associated with growth of both melanoma and fibrosarcoma tumors. The dose for loratadine in this study was 10 mg/day.

Thus, it would be particularly desirable to find methods of treatment with the advantages of known non-sedating antihistamines which would not have the aforementioned disadvantages.

3. SUMMARY OF THE INVENTION

The present invention provides methods and compositions involving descarboethoxyloratadine, i.e., 8-chloro-6,11-dihydro-11-(4-piperidylidene)-5H-benzo[5,6]cyclohepta[1,2-b]pyridine ("DCL"). This compound is specifically described in Quercia, et al. *Hosp. Formul.*, 28: 137–53 (1993) and U.S. Pat. No. 4,659,716.

In one aspect, this invention provides, a method of treating allergic asthma in a human while avoiding the concomitant liability of adverse side-effects associated with the administration of non-sedating antihistamines, comprising administering to a human a composition, said composition comprising (i) a therapeutically effective amount of DCL or a pharmaceutically acceptable salt thereof; (ii) a therapeutically effective amount of a decongestant; and a pharmaceutically acceptable carrier.

The invention also provides a method of treating allergic asthma in a human while avoiding the concomitant liability of adverse side-effects associated with the administration of non-sedating antihistamines, comprising administering to a human a composition, said composition comprising (i) a therapeutically effective amount of DCL or a pharmaceutically acceptable salt thereof; (ii) a leukotriene inhibitor selected from the group consisting of 5-lipoxygenase inhibitors, 5-lipoxygenase activating protein antagonists, and leukotriene $D_4$ antagonists; and a pharmaceutically acceptable carrier.

This invention is also directed to a method of treating allergic asthma in a human while avoiding the concomitant liability of adverse side-effects associated with the administration of non-sedating antihistamines, comprising administering to a human a therapeutically effective amount of DCL and a therapeutically effective amount of a decongestant.

Additionally, this invention provides for a method of treating allergic asthma in a human while avoiding the concomitant liability of adverse side-effects associated with the administration of non-sedating antihistamines, comprising administering to a human a therapeutically effective amount of DCL and a therapeutically effective amount of a leukotriene inhibitor.

This invention also provides for a method of treating dermatitis in a human while avoiding the concomitant liability of adverse side-effects associated with the administration of non-sedating antihistamines, comprising administering to a human a therapeutically effective amount of DCL or a pharmaceutically acceptable salt thereof.

4. DETAILED DESCRIPTION OF THE INVENTION

The present invention encompasses a method of treating allergic asthma in a human while avoiding the concomitant liability of adverse side-effects associated with the administration of non-sedating antihistamines, comprising administering to a human a composition, said composition comprising (i) a therapeutically effective amount of DCL or a pharmaceutically acceptable salt thereof; (ii) a therapeutically effective amount of a decongestant; and a pharmaceutically acceptable carrier. DCL and a decongestant may also be administered separately in the method of treating allergic asthma. For example, DCL and a decongestant may be administered concurrently or sequentially, i.e., DCL and a decongestant may be administered in combination either concurrently or by the sequential administration of DCL and decongestant or the sequential administration of a decongestant and DCL.

Thus, the present invention also encompasses a method of treating allergic asthma in a human while avoiding the concomitant liability of adverse side-effects associated with the administration of non-sedating antihistamines, comprising administering to a human a therapeutically effective amount of DCL and a therapeutically effective amount of a decongestant.

The present invention also relates to a method of treating allergic asthma in a human while avoiding the concomitant liability of adverse side-effects associated with the administration of non-sedating antihistamines, comprising administering to a human a composition, said composition comprising (i) a therapeutically effective amount of DCL or a pharmaceutically acceptable salt thereof; (ii) a therapeutically effective amount of a leukotriene inhibitor selected from the group consisting of 5-lipoxygenase ("5-LO") inhibitors, 5-lipoxygenase activating protein ("FLAP") antagonists, and leukotriene $D_4$ ("$LTD_4$") antagonists; and a pharmaceutically acceptable carrier. The administration of DCL and a leukotriene inhibitor in the methods of the present invention for treating allergic asthma may be either concurrently or sequentially, i.e., DCL and a leukotriene inhibitor may be administered as a combination, concurrently but separately, or by the sequential administration of DCL and leukotriene inhibitor or the sequential administration of a leukotriene inhibitor and DCL.

Thus, the present invention encompasses a method of treating allergic asthma in a human while avoiding the concomitant liability of adverse side-effects associated with the administration of non-sedating antihistamines, comprising administering to a human a therapeutically effective amount of DCL and a therapeutically effective amount of a leukotriene inhibitor.

A further aspect of the present invention includes a method of treating dermatitis in a human while avoiding the concomitant liability of adverse side-effects associated with the administration of non-sedating antihistamines, comprising administering to a human a therapeutically effective amount of DCL or a pharmaceutically acceptable salt thereof.

The side-effects to be avoided by the methods of the present invention include but are not limited to, cardiac arrythmia and tumor promotion. It has been found that when DCL is concurrently administered with a drug that inhibits cytochrome P450 including but not limited to ketoconazole, itraconazole, erythromycin and others known by those skilled in the art, the drug-drug interactions are decreased in comparison to the concurrent administration of loratadine or other non-sedating antihistamines with said drug. Thus, the methods of the present invention as described above are particularly useful in the treatment of allergic disorders such as dermatitis and asthma in a human having a higher than normal propensity for or incidence of cancer and/or while avoiding interaction with a drug that inhibits cytochrome P450.

The present invention also includes novel compositions for use in the methods described above.

It has been found that DCL is at least about twenty times more potent at the histamine receptor when compared to loratadine. Thus, the dosage range by the modes of administration described herein and for use in the methods of the present invention, are about 0.1 to less than about 10 mg per day. This dosage range is significantly lower than what has been recommended for other non-sedating antihistamines, including loratadine which has a recommended oral dose of 5 to 100 mg per day. However, due to the significantly less side-effects, DCL can be given in doses higher than those suggested for loratadine thereby offering an improved therapeutic range than loratadine.

Loratadine and other non-sedating antihistamines have antihistaminic activity and provide therapy and a reduction of symptoms for a variety of conditions and disorders related to allergic rhinitis and other allergic disorders, diabetes mellitus and other conditions; however, such drugs, while offering the expectation of efficacy, cause adverse side-effects. Utilizing DCL results in clearer dose-related definitions of efficacy, diminished adverse side-effects, and accordingly, an improved therapeutic index. It is, therefore, more desirable to use DCL than to use loratadine itself or other non-sedating antihistamines.

The term "adverse effects" includes, but is not limited to tumor promotion, cardiac arrhythmias, cardiac conduction disturbances, appetite stimulation, weight gain, sedation, gastrointestinal distress, headache, dry mouth, constipation, and diarrhea. The term "cardiac arrhythmias" includes, but is not limited to ventricular tachyarrhythmias, torsades de pointes, and ventricular fibrillation.

The phrase "therapeutically effective amount" means that amount of DCL which provides a therapeutic benefit in the treatment or management of allergic disorders such as urticaria, allergic rhinitis, symptomatic dermographism, dermatitis, allergic asthma, retinopathy or other small vessel disorders associated with diabetes mellitus, and the symptoms associated with allergic rhinitis such as cough, cold, cold-like, and/or flu symptoms including, but not limited to, sneezing, rhinorrhea, lacrimation, and dermal irritation.

The term "allergic asthma" is defined as a disorder characterized by increased responsiveness of the trachea and bronchi to various stimuli which results in symptoms which include wheezing, cough, and dyspnea.

The term "dermatitis" is that disorder caused by inflammation to the skin including endogenous and contact dermatitis such as, but not limited to: actinic dermatitis (or photodermatitis), atopic dermatitis, chemical dermatitis, cosmetic dermatitis, dermatitis aestivalis, and seborrheic dermatitis.

The term "leukotriene inhibitor" includes any agent or compound that inhibits, restrains, retards or otherwise interacts with the action or activity of leukotrienes, such as, but not limited to, 5-lipoxygenase ("5-LO") inhibitors, 5-lipoxygenase activating protein ("FLAP") antagonists, and leukotriene $D_4$ ("$LTD_4$") antagonists.

The term "5-lipoxygenase inhibitor" or "5-LO inhibitor" includes any agent or compound that inhibits, restrains, retards or otherwise interacts with the enzymatic action of 5-lipoxygenase, such as, but not limited to, zileuton, docebenone, piripost, and ICI-D2318.

The term "5-lipoxygenase activating protein antagonist" or "FLAP antagonist" includes any agent or compound that inhibits, restrains, retards or otherwise interacts with the action or activity of 5-lipoxygenase activating protein, such as, but not limited to MK-591 and MK-886.

The term "leukotriene $D_4$ antagonist" or "$LTD_4$ antagonist" includes any agent or compound that inhibits, restrains, retards or otherwise interacts with the action or activity of leukotriene $D_4$, such as but not limited to zarfirlukast (ICI-204219).

The magnitude of a prophylactic or therapeutic dose of DCL in the acute or chronic management of an allergic disorder or condition will vary with the severity of the condition to be treated and the route of administration. The dose, and perhaps the dose frequency, will also vary according to the age, body weight, and response of the individual patient. Suitable total daily dose ranges can be readily determined by those skilled in the art. In general, the total daily dose range for DCL, for the conditions described herein, is from about 0.1 mg to less than about 10 mg administered in single or divided doses orally, topically, transdermally, or locally by inhalation. For example, a preferred oral daily dose range should be from about 0.1 mg to about 5 mg. A more preferred oral dose is about 0.2 mg to about 1 mg. A preferred oral daily dose range of decongestant, such as pseudoephedrine, should be from about 50 mg to about 300 mg, more preferably, about 150 mg to about 250 mg. In addition, suitable oral daily dosage ranges of leukotriene inhibitor can be readily determined by those skilled in the art.

It is further recommended that children, patients aged over 65 years, and those with impaired renal or hepatic function initially receive low doses, and that they then be titrated based on individual response(s) or blood level(s). It may be necessary to use dosages outside these ranges in some cases as will be apparent to those skilled in the art. Further, it is noted that the clinician or treating physician will know how and when to adjust, interrupt, or terminate therapy in conjunction with individual patient response.

The term "therapeutically effective amount of DCL or a pharmaceutically acceptable salt thereof" is encompassed by the above-described dosage amounts. In addition, the terms "said composition comprising (i) a therapeutically effective amount of DCL or a pharmaceutically acceptable salt thereof; and (ii) a therapeutically effective amount of a decongestant"; and "said composition comprising (i) a therapeutically effective amount of DCL or a pharmaceutically acceptable salt thereof; and (ii) a therapeutically effective amount of a leukotriene inhibitor" are also encompassed by the above-described dosage amounts and dose frequency schedule.

Any suitable route of administration may be employed for providing the patient with an effective dosage of DCL according to the methods of the present invention. For example, oral, intraoral, rectal, parenteral, epicutaneous, transdermal, subcutaneous, intramuscular, intranasal, sublingual, intradural, intraocular, intrarespiratory, oral or nasal inhalation and like forms of administration may be employed. For the methods to treat dermatitis topical administration is preferred.

The pharmaceutical compositions used in the methods of the present invention comprise DCL, the metabolic derivative of loratadine, as active ingredient, or a pharmaceutically acceptable salt thereof, and may also contain a pharmaceutically acceptable carrier, and optionally, other therapeutic ingredients.

The term "pharmaceutically acceptable salt" refers to a salt prepared from pharmaceutically acceptable non-toxic acids or bases including inorganic acids or bases or organic acids or bases. Examples of such inorganic acids are hydrochloric, hydrobromic, hydroiodic, sulfuric, and phosphoric. Appropriate organic acids may be selected, for example, from aliphatic, aromatic, carboxylic and sulfonic classes of organic acids, examples of which are formic, acetic, propionic, succinic, glycolic, glucuronic, maleic, furoic, glutamic, benzoic, anthranilic, salicylic, phenylacetic, mandelic, embonic (pamoic), methanesulfonic, ethanesulfonic, pantothenic, benzenesulfonic, stearic, sulfanilic, algenic, and galacturonic. Examples of such inorganic bases include metallic salts made from aluminum, calcium, lithium, magnesium, potassium, sodium, and zinc. Appropriate organic bases may be selected, for example, from N,N-dibenzylethylenediamine, chloroprocaine, choline, diethanolamine, ethylenediamine, meglumaine (N-methylglucamine), lysine and procaine.

The compositions for use in the methods of the present invention can include suitable excipients or carriers such as starches, sugars, microcrystalline cellulose, diluents, granulating agents, lubricants, binders, disintegrating agents, and the like.

Dosage forms include tablets, troches, dispersions, suspensions, solutions, capsules, patches, syrups, elixirs, gels, powders, magmas, lozenges, ointments, creams, pastes, plasters, lotions, discs, suppositories, nasal or oral sprays, aerosols and the like.

Because of their ease of administration, tablets and capsules represent the most advantageous oral dosage unit form, in which case solid pharmaceutical carriers are employed. If desired, tablets may be coated by standard aqueous or nonaqueous techniques.

In addition to the common dosage forms set out above, the compound for use in the methods of the present invention may also be administered by controlled release means and/or delivery devices such as those described in U.S. Pat. Nos. 3,845,770; 3,916,899; 3,536,809; 3,598,123; and 4,008,719, the disclosures of which are hereby incorporated by reference.

Pharmaceutical compositions for use in the methods of the present invention may be prepared by any of the methods of pharmacy, but all methods include the step of bringing into association the active ingredient with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation.

For example, a tablet may be prepared by compression or molding, optionally, with one or more accessory ingredients. Compressed tablets may be prepared by compressing in a suitable machine the active ingredient in a free-flowing form such as powder or granules, optionally mixed with a binder, lubricant, inert diluent, surface active or dispersing agent. Molded tablets may be made by molding, in a suitable machine, a mixture of the powdered compound moistened with an inert liquid diluent. Desirably, each tablet contains from about 0.1 mg to less than about 10 mg of the active ingredient, and each cachet or capsule contains from about 0.1 mg to about less than 10 mg of the DCL.

The invention is further defined by reference to the following examples describing in detail the preparation of the compound and the compositions used in the methods of the present invention, as well as their utility. It will be apparent to those skilled in the art that many modifications, both to materials and methods, may be practiced which are within the scope of this invention.

5. EXAMPLES

5.1 Example 1
Preparation of loratadine and its metabolites

Loratadine can be synthesized by methods disclosed in U.S. Pat. No. 4,282,233. The metabolites are prepared similarly, by reaction steps conventional in the art, as described in U.S. Pat. No. 4,659,716 which is incorporated here by reference in its entirety. One common method of preparing DCL is to reflux loratadine in the presence of sodium hydroxide and ethanol as depicted below.

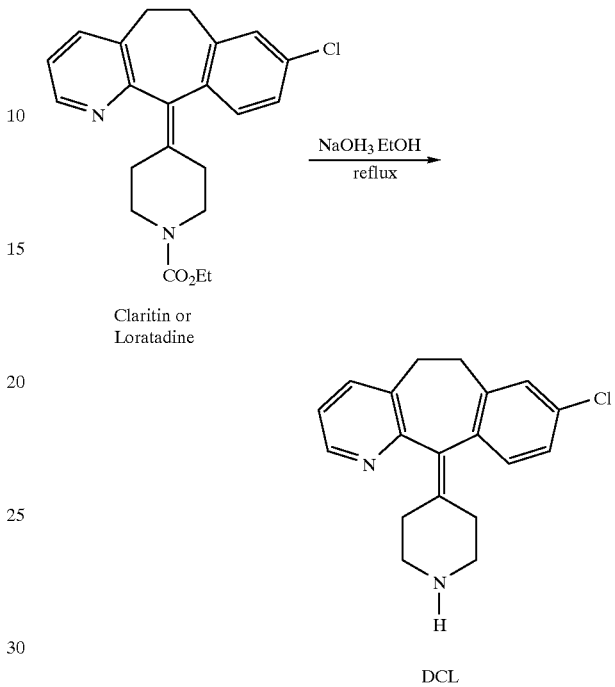

Extraction of Commercially Available Claritin Tablets (600× 10 mg)

Tablets of loratadine, were diluted with water and chloroform. The mixture was stirred, then filtered through celite, rinsed with chloroform until the filtrate contained no loratadine. The separated aqueous layer was extracted with chloroform twice. The combined organic layer was washed with water, brine and dried over sodium sulfate. The solvent was evaporated to give pure loratadine as a white solid.

Saponification of loratadine

Loratadine (4.0 g) was added to a solution of sodium hydroxide (5.9 g) in 280 mL of absolute ethanol and the mixture was stirred at reflux for four days. The mixture was cooled and concentrated to remove ethanol. The residue was diluted with water and aqueous layer was extracted with methylene chloride five times. The combined organic layer was washed with water, brine and dried over sodium sulfate. The solvent was evaporated to give 2.82 g (87%) of pure loratadine derivative (or metabolite) as a pale-tan solid.

5.2 Example 2
Antihistaminic Activity

The antihistaminic activity of loratadine and DCL were compared in isolated strips of guinea pig ileum contracted with histamine. This preparation is generally accepted by those skilled in the art as predicative of its efficacy as a peripheral histamine H-1 receptor.

Methods

Experiments were performed on pieces of ileum taken from male guinea pigs (Hartley strain, 419–560 grams; Elm Hill Breeding Laboratories, Chelmsford, Mass.). The tissues were suspended in tissue chambers containing 40 ml of Tyrode's solution aerated with 95% oxygen and 5% carbon dioxide at 35° C. The Tyrode's solution contained (in mM) 137 NaCl, 2.7 KCl, 2.2 $CaCl_2$, 0.025 $MgCl_2$, 0.4 $NaHPO_4$, 11.9 NaHCO$_3$ and 5.5 glucose. Contractions in response to histamine were recorded with isotonic transducers (Model 357, Harvard Apparatus Company, South Natick, Mass.) using an ink-writing polygraph (Model 7, Grass Instrument Company, Quincy, Mass.). A tension of one gram was maintained on all tissues at all times.

In each experiment three or four pieces of ileum were removed from a single animal, suspended in individual tissue chambers and allowed to equilibrate with the bathing solution for one hour before the administration of any drugs. In four initial experiments in which tissues were exposed to histamine at concentrations of 1×10$^{-7}$, 1×10$^{-6}$ and 1×10$^{-5}$ mol/l, histamine at 1×10$^{-6}$ mol/l produced strong contractions on the linear portion of the log-concentration-effect curve and this concentration of histamine was chosen for use in all further experiments.

For determining the antihistaminic effects of loratadine and DCL, tissues were exposed briefly (about 15 seconds) to 1×10$^{-6}$ mol/l of histamine at intervals of 15 minutes. After two successive exposures to histamine produced contractions of approximately the same magnitude, loratadine or DCL, at final concentrations that varied three- or ten-fold, was added to all but one of the tissue chambers, the untreated tissue serving as a control for the treated tissues. After each exposure of drug-treated tissues to histamine, the fluid in the tissue chamber was replaced with fluid free of histamine but containing the same drug at the same concentration. The histamine challenges were made at 5, 20, 35, 50, 65, 80, 95, 110 and 125 minutes of exposure to the drug or at comparable times in the control tissues.

Subsequent analyses of the results from each experiment involved (i) normalization of the data from each tissue for differences in inherent contractility by expressing all contractions as a percent of the last predug contraction, (ii) normalization of the data for possible time-related changes in contractility by expressing the contractions recorded during drug-exposure as a percent of the corresponding value for the untreated tissue, and finally (iii) calculation of the drug-related percent reduction of each contraction.

The resultant sets of data for drug concentration and corresponding percent reduction in histamine-response were then used to estimate for each experiment the concentration of drug that would have produced a 50 percent reduction in the histamine response, the IC$_{50}$. This was done by fitting straight lines to the data using the method of least squares and calculating the IC$_{50}$ from the equation of the line. The mean ± standard error of the values for the experiments on each drug were calculated, and differences between the drugs was examined using the Kruskal Wallis 1-way analysis of variance by ranks.

A summary of the results are shown in the following two tables. The percentages of reduction of histamine-induced contractions of the isolated guinea pig ileum produced by exposure for 125 minutes to various concentrations of each drug are set forth below:

TABLE 1

| | | Reduction of Histamine-induced Guinea Pia Ileum Contractions (Percent) | | | | | |
|---|---|---|---|---|---|---|---|
| | Expt | Concentration of drug (mol/l) | | | | | |
| Drug | No. | 3 × 10$^{-10}$ | 1 × 10$^{-9}$ | 3 × 10$^{-9}$ | 1 × 10$^{-8}$ | 3 × 10$^{-8}$ | 1 × 10$^{-7}$ |
| Loratadine | 1 | — | 19.05 | — | 13.33 | — | 88.57 |
| | 2 | — | — | — | 28.32 | 54.42 | 98.66 |
| | 3 | — | — | — | 39.64 | 44.68 | 93.38 |
| | 4 | — | — | — | 55.86 | 45.83 | 86.46 |
| DCL | 1 | 11.93 | 73.12 | | | | |
| | 2 | 38.91 | 38.81 | 56.71 | | | |
| | 3 | 40.00 | 62.69 | 76.21 | | | |
| | 4 | 35.43 | 44.13 | 76.43 | | | |

TABLE 2

| | Reduction of Histamine-induced Guinea Pig Icum Contractions (IC$_{50}$) | |
|---|---|---|
| Drug | Expt | IC$_{50}$(M) |
| Loratadine | 1 | 1.90 × 10$^{-8}$ |
| | 2 | 2.21 × 10$^{-8}$ |
| | 3 | 2.10 × 10$^{-8}$ |
| | 4 | 1.22 × 10$^{-8}$ |
| | Mean | 1.86 × 10$^{-8}$ |
| | S.E. | 0.22 |
| DCL | 1 | 6.36 × 10$^{-10}$ |
| | 2 | 19.2 × 10$^{-10}$ |
| | 3 | 5.26 × 10$^{-10}$ |
| | 4 | 8.66 × 10$^{-10}$ |
| | Mean | 9.75 × 10$^{-10}$ |
| | S.E. | 3.20 |

Note:
There is a statistically significant drug-related difference in IC$_{50}$ values (P = 0.0209).

These results indicate that DCL is approximately 20 fold more potent at the histamine receptor than loratadine.

5.3 Example 3

Receptor binding studies

Receptor binding studies on the binding affinities of loratadine and DCL at histamine H-1 receptors were performed.

The methods described by Dini et al., which is hereby incorporated by reference herein (Agents and Actions, 33: 181–184, 1991), were used for these binding studies. Guinea pig cerebella membranes were incubated with 0.5 nM 3H-pyrilamine for 10 min at 25° C. Following incubation, the assays were rapidly filtered under vacuum through GF/B glass fiber filters (Whatman) and washed several times with ice-cold buffer using a Brandel Cell Harvester. Bound radioactivity was determined with a liquid scintillation counter (LS 6000, Beckman) using a liquid scintillation cocktail (Formula 989, DuPont NEN).

$IC_{50}$ values were determined for compounds tested and pyrilamine at the H-1 histamine receptor:

TABLE 3

Inhibition of Pyrilamine Binding at H-1 Receptor

| Compound | H-1 receptor $IC_{50}$(nM) | (nH) |
|---|---|---|
| Loratadine | 721 | (1.55) |
| DCL | 51.1 | (1.12) |
| Pyrilamine | 1.4 | (0.98) |

As shown above, DCL was found to have a 14 fold greater affinity than loratadine for histamine H-1 receptors. These results are consistent with the findings demonstrating a higher potency of DCL over loratadine for inhibition of histamine-induced contractions of guinea pig ileum.

These studies confirm that DCL has a higher potency for histamine receptors than loratadine.

5.4 Example 4
Tumor Promoting Activity

Inhibition of lymphocyte mitogenesis was used to screen the potencies of loratadine and DCL as tumor promoting agents.

Mitogenesis studies

Fresh spleen cells ($5 \times 10^5$) obtained from 5-week old BALB/c mice (Charles River, ST. Constant, PQ) were suspended in RPMI 1640 medium containing 2% fetal calf serum (Grand Island Biological Co., Grand Island, N.Y.) seeded into replicate microwell plates (Nunc) to which concanavalin (Con) A (2 $\mu$g/ml; Sigma Chemical Co., St. Louis, Mo.) was added and incubated (37° C., 95% air, 5% $CO_2$) in the absence or presence of increasing concentrations of the test agents dissolved in saline or other vehicles. Forty-three hours after the addition of Con A, 0.25 nmol $^3$H-thymidine (6.7 Ci/nmol; ICN Radiopharmaceuticals, Montreal, PQ) was added to each well. After an additional 5-hour incubation, the cells were washed from the wells onto filter papers employing an automated cell sorter. The filters were placed into vials containing 5 ml scintillation fluid (Readysafe; Beckman), and radioactivity incorporated into DNA at 48 hours was determined (n=3). $IC_{50}$ values for inhibition of mitogenesis were determined over wide range of concentrations (0.1 to 10 $\mu$M).

TABLE 4

Inhibition of Concanavalin A Induced Stimulation of Lymphocytes ($IC_{50}$)

| Loratadine | 1.0 $\mu$M |
|---|---|
| DCL | 5.6 $\mu$M |

These results indicate that DCL is 5–7 fold less active than loratadine at promoting tumor growth.

5.5 Example 5
Cardiovascular Effects

The effects of DCL on cardiac potassium currents were studied.

Methods

Single ventricular myocytes of the guinea-pig and the rabbit were dissociated by enzymatic dispersion (see Carmeliet, *J. Pharmacol. Exper. Ther.*, 1992, 262, 809–817 which is incorporated herein by reference in its entirety). The single suction patch electrode, with a resistance of 2 to 5M$\Omega$ was used for voltage clamp (Axoclamp 200 A). P-clamp software (Axon Instruments) was used to generate voltage-clamp protocols and to record and analyze data. The standard solution contained in mM: NaCl 137.6, KCl 5.4, $CaCl_2$ 1.8, $MgCl_2$ 0.5, HEPES 11.6 and glucose 5, and NaOH was added to pH 7.4. The intracellular solution contained KCl 120, $MgCl_2$ 6, $CaCl_2$ 0.154, $Na_2$ATP 5, EGTA 5, and HEPES 10, with KOH added until pH 7.2.

Effect on the delayed rectifying $K^+$ current. ($I_{kr}$) in rabbit ventricular myocytes The voltage clamp protocol consisted of clamps from a holding potential of −50 mV to +10 mV for a duration of 4 sec. The change in tail current was measured as a function of the drug concentration. This concentration was changed between $10^{-7}$ and $10^{-5}$M in five steps. Exposure to each concentration lasted 15 min. At the end, washout was attempted during 30 min.

Effect on the inward rectifier current in guinea-pig myocytes

The inward rectifier was measured by applying ramp voltage clamps starting from −50 mV and hyperpolarizing the membrane to −120 mV at a speed of 10 mV/sec. The starting concentration was the 50% efficiency concentration, determined in the preceding experiments. Higher concentrations were applied if this initial concentration was without effect.

Effect on IK, in guinea-pig ventricular myocytes

Tail currents were measured following depolarizing clamps of 2 sec duration to potentials between −30 mV and +60 mV; holding potential −50 mV.

The results from these studies indicate that DCL is less active than terfenadine in inhibiting the cardiac delayed rectifier and thus has no potential for cardiac side-effects.

Thus, the methods of the present invention are less toxic than methods which use other non-sedating antihistamines.

5.6 Example 6
Inhibition of cytochrome P450

This study is conducted to determine the extent that loratadine and DCL inhibit human cytochrome P4503A4 (CYP3A4). CYP3A4 is involved in many drug-drug interactions and quantitation of inhibition of CYP3A4 by loratadine or DCL indicates the potential of such drug-drug interactions. Inhibition is measured using the model substrate testosterone and cDNA-derived CYP3A4 in microsomes prepared from a human lymphoblastoid cell line designated h3A4v3.

Study Design

The inhibition study consists of the determination of the 50% inhibitory concentration ($IC_{50}$) for the test substance. A single testosterone concentration (120 $\mu$M, approximately twice the apparent Km) and ten test substance concentrations, separated by approximately ½ log, are tested in duplicate. Testosterone metabolism is assayed by the production of the 6($\beta$)-hydroxytestosterone metabolite. This metabolite is readily quantitated via HPLC separation with absorbance detection.

Storage/Preparation of the test substances and addition to the incubations

The test substances will be stored at room temperature. The test substances will be dissolved in ethanol for addition to the incubations. The solvent concentration will be constant for all concentrations of the test substance.

$IC_{50}$ Determination

Final test substance concentrations will be 100, 30, 10, 3, 1, 0.3, 0.1, 0.03, 0.01, 0.003 and 0 $\mu$M. Each test concentration will be tested in duplicate incubations in accordance with the method below:

13

Method

A 0.5 ml reaction mixture containing 0.7 mg/ml protein, 1.3 mM NADP+, 3.3 mM glucose-6-phosphate, 0.4 U/ml glucose-6-phosphate dehydrogenase, 3.3 mM magnesium chloride and 120 µM testosterone in 100 mM potassium phosphate (pH 7.4) will be incubated at 37° C. for 30 min. A known quantity of 11(β)-hydroxytestosterone will be added as an internal standard to correct for recovery during extraction. The reaction mixture will be extracted with 1 ml methylene chloride. The extract will be dried over anhydrous magnesium sulfate and evaporated under vacuum. The sample will be dissolved in methanol and injected into a 4.6×250 mm 5u C18 HPLC column and separated at 50° C. with a mobile phase methanol/water at a flow rate of 1 ml per min. The retention times are approximately 6 min for the 6(β)-hydroxy, 8 min for 11(~)-hydroxy and 12 min for testosterone. The product and internal standard are detected by their absorbance at 254 nm and quantitated by correcting for the extraction efficiency using the absorbance of the 11(β)-hydroxy peak and comparing to the absorbance of a standard curve for 6(β)-hydroxytestosterone.

Data reporting

For each test substance, the concentration of 6(β)-hydroxytestosterone metabolite in each replicate incubation is determined and the percentage inhibition relative to solvent control is calculated. The $IC_{50}$ is calculated by linear interpolation.

Useful pharmaceutical dosage forms for administration of the compounds used in the methods of the present invention can be illustrated as follows:

5.7. Example 7

Capsules

A large number of unit capsules are prepared by filling standard two-piece hard gelatin capsules each with 0.1 to 10 milligrams of powdered active ingredient, 150 milligrams of lactose, 50 milligrams of cellulose, and 6 milligrams magnesium stearate.

5.8. Example 8

Soft Gelatin Capsules

A mixture of active ingredient in a digestible oil such as soybean oil, lecithin, cottonseed oil or olive oil is prepared and injected by means of a positive displacement pump into gelatin to form soft gelatin capsules containing 0.1 to 10 milligrams of the active ingredient. The capsules are washed and dried.

5.9 Example 9

Tablets

A large number of tablets are prepared by conventional procedures so that the dosage unit was 0.1 to 10 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

Various modifications of the invention in addition to those shown and described herein will be apparent to those skilled in the art from the foregoing description. Such modifications are also intended to fall within the scope of the appended claims.

The foregoing disclosure includes all the information deemed essential to enable those skilled in the art to practice the claimed invention. Because the cited patents or publications may provide further useful information these cited materials are hereby incorporated by reference in their entireties.

What is claimed is:

1. A method of treating allergic asthma in a human while avoiding the concomitant liability of adverse side-effects associated with the administration of non-sedating antihistamines, comprising administering to a human a composition, said composition comprising (i) a therapeutically effective amount of DCL or a pharmaceutically acceptable salt thereof; (ii) a therapeutically effective amount of leukotriene inhibitor selected from the group consisting of 5-lipoxygenase inhibitors, 5-lipoxygenase activating protein antagonists, and leukotriene $D_4$ antagonists; and a pharmaceutically acceptable carrier.

2. A method of treating dermatitis in a human while avoiding the concomitant liability of adverse side-effects associated with the administration of non-sedating antihistamines, comprising administering to a human a therapeutically effective amount of DCL or a pharmaceutically acceptable salt thereof.

3. The method of claim 1 or 2 wherein said adverse side-effect is cardiac arrhythmia or tumor promotion.

4. The method of claim 1 or 2 wherein the human has a higher than normal propensity for a incidence of cancer.

5. The method of claim 1 or 2 wherein interaction with a drug that inhibits cytochrome P450 is avoided.

6. The method of claim 1 or 2 wherein the amount of DCL administered is from about 0.1 mg to less than about 10 mg per day.

7. The method of claim 6 wherein the amount of DCL administered is from about 0.1 mg to about 5 mg per day.

8. The method of claim 1 or 2 wherein the compositions are administered as a nasal or oral spray.

9. A method of treating allergic asthma in a human while avoiding the concomitant liability of adverse side-effects associated with the administration of non-sedating antihistamines, comprising administering to a human a therapeutically effective amount of DCL and a therapeutically effective amount of a leukotriene inhibitor.

10. The method of claim 9 wherein the DCL is administered as a nasal or oral spray.

11. A pharmaceutical composition which comprises a therapeutically effective amount of DCL and a therapeutically effective amount of a leukotriene inhibitor selected from the group consisting of 5-lipoxygenase inhibitors, 5-lipoxygenase activating protein antagonists, and leukotriene $D_4$ antagonists.

12. The composition of claim 11 wherein said 5-lipoxygenase inhibitor is zileuton.

13. The composition of claim 11 wherein said 5-lipoxygenase inhibitor is docebenone.

14. The composition of claim 11 wherein said 5-lipoxygenase inhibitor is piripost.

15. The composition of claim 11 wherein said 5-lipoxygenase inhibitor is ICI-D2318.

16. The composition of claim 11 wherein said 5-lipoxygenase activating protein is MK-591.

17. The composition of claim 11 wherein said 5-lipoxygenase activating protein is MK-886.

18. The composition of claim 11 wherein said leukotriene $D_4$ antagonist is zarfirlukast.

\* \* \* \* \*